(12) United States Patent
Simard

(10) Patent No.: US 6,237,600 B1
(45) Date of Patent: May 29, 2001

(54) REUSABLE ABSORBENT SURGICAL DRAPE

(75) Inventor: Francois Simard, Granby (CA)

(73) Assignee: Stedfast Inc., Granby (CA)

( * ) Notice: Subject to any disclaimer, the term of this patent is extended or adjusted under 35 U.S.C. 154(b) by 0 days.

(21) Appl. No.: 09/398,532

(22) Filed: Sep. 16, 1999

(30) Foreign Application Priority Data

Sep. 16, 1998 (CA) .................................................. 2247577

(51) Int. Cl.⁷ .................................................. A61B 19/00
(52) U.S. Cl. ............................................ 128/849; 427/245
(58) Field of Search ............................ 128/849; 427/245, 427/358, 365

(56) References Cited

U.S. PATENT DOCUMENTS 5,846,604 * 12/1998 Caldwell .

* cited by examiner

Primary Examiner—Michael A. Brown
Assistant Examiner—Lalita M. Hamilton
(74) Attorney, Agent, or Firm—Eric Fincham

(57) ABSTRACT

There is provided a surgical drape of a multilayer structure, the surgical drape having an inner layer of polyurethane material which is substantially impervious to material passing therethrough while being vapor permeable, a top layer of a knit fabric having interstices therebetween to absorb moisture, and a bottom layer of a knit fabric. The drape preferably has a thickness of between 0.015 inches and 0.034 inches.

7 Claims, No Drawings

REUSABLE ABSORBENT SURGICAL DRAPE

The present invention relates to surgical drapes and more particularly, relates to a reusable surgical drape.

BACKGROUND OF THE INVENTION

Surgical drapes are widely used during medical procedures and have gradually evolved over the years following the recognition that certain pathological agents posed a health threat to operating room personnel. As a result, surgical drapes which provide a sterile barrier between the non-sterile patient and the sterile operating room personnel and instruments were considered desirable.

Originally, a polycotton fabric which is a blend of polyester and cotton was used as the fabric of choice for surgical drapes. The one major drawback to this material was its lack of impermeability. In order to minimize the potential problems, a number of layers were used which did provide a certain minimal degree of protection. However, the required thickness as well as the high cost of sterilizing with the attendant wear and tear was recognized.

Subsequently, disposable surgical drapes were proposed in the art and they offered the advantage of impermeability. These disposable drapes became extremely popular and although the cost is substantial, the benefit of the impermeable barrier has been considered sufficiently important that their continued use has prevailed.

A disadvantage of the disposable surgical drape is the "slippery" finish on the surface. Typically, any liquid on the upper layer is permitted to move to pockets or the like which are formed at the edges of the drape. The drape is generally recognized 25 being deficient in that the slippery top surface is of a nature such that materials such as operating room instruments can not be placed thereon. Similarly, the bottom surface can be slippery thus permitting movement of the drape.

SUMMARY OF THE INVENTION

It is an object of the present invention to provide a surgical drape which overcomes the above disadvantages.

According to one aspect of the present invention, there is provided a surgical drape of a multilayer structure, the surgical drape comprising an inner layer of a polyurethane material, the polyurethane material being substantially impervious to bacteria passing therethrough, the polyurethane layer being vapor permeable; a top layer of a knit fabric, the layer of knit fabric having interstices therebetween to absorb moisture; and a bottom layer of a knit fabric.

DESCRIPTION OF THE PREFERRED EMBODIMENTS

Generally, there is provided a middle layer which acts as the barrier membrane. This middle layer is preferably formed of a polyurethane material and more preferably, is a 30 μm microporous polyurethane. Naturally, this material is thin since it must also be permeable to water vapor in order to provide for sterilization.

The upper or top layer is formed of an absorbent material. This material also has a non-slippery surface. Preferably, it is made of a polyester warp knit fabric. The special knit has a structure which acts as an active sponge. Although the material itself may be treated to have a hydrophilic nature, the liquid is stored in the voids of the multifilament yarn.

The bottom surface is also formed of a tricot polyester warp knit which is designed to be light.

The three components are laminated with a finely dispersed polyurethane adhesive on each side of the membrane. The polyurethane is applied in an adhesive dispersion pattern which permits vapor to pass through the membrane.

The surgical drape is designed to be flame resistant and as such, known methods of achieving such flame retardancy may be used from the incorporation of flame retardant compounds therein.

As a surgical drape, the product must be substantially impervious to biological penetration. This is achieved through the use of the intermediate polyurethane layer which preferably has a thickness of between 20 μm and 40 μm and also is of a microporous structure. As such, the layer must be water vapor permeable to permit sterilization thereof and preferably, the polyurethane layer is of a microporous structure having a uniform pore size in the order of 1 micron.

EXAMPLE 1

A sample of a surgical drape was prepared using a polyurethane inner layer and a polyester knit layer on either side thereof. The three components were laminated with a finely dispersed polyurethane adhesive on each side of the polyurethane. The total thickness of the surgical drape varied between 0.026 inch and 0.028 inch The material was subjected to a biological penetration test which comprised ASTM F1671/97A which comprised an exposure of the material for 5 minutes at 0 psig, 1 minute at 2 psig, and 54 minutes at 0 psig. The material had no signs of biological penetration (the fluid contained $4.01 \times 10^8$ plaque forming units (pfu)/ml).

Four samples were tested and in each case, the number of pfu/ml on the collection side assay was less than one.

The above test was repeated with a surgical drape sample formed according to the parameters previously set out but with a thickness of 0.021 inch. Again, there was less than 1 pfu/ml.

Three tests were run on a sample of the surgical drape material having a thickness of 28 mil. The test was conducted according to ASTM F903 with the liquid being a synthetic blood. The test comprised 5 minutes at ambient pressure, 1 minute at 2 psig, and 54 minutes at ambient pressure. There was no indication of passage through the material.

The test set forth above was conducted on a sample having a thickness of 21 mil. Three samples were tested. Again, there was no indication of any fluid passage through the layer.

The fabric forming the surgical drape preferably has a weight of 5 plus or minus one half ounce per yard squared. The water vapor diffusion according to ASTM E 96 method BW is preferably in the order of at least 3,500 grams/meter$^2$/ 24 hours.

It will be understood that the above described embodiment is for purposes of illustration only and that changes and modifications may be made thereto without departing from the spirit and scope of the invention.

I claim:

1. A surgical drape of a multilayer structure, said surgical drape comprising:
    an inner layer of a polyurethane material, said polyurethane material being substantially impervious to bacteria passing therethrough, said polyurethane layer being vapor permeable;
    a top layer of a knit fabric adhesively secured to a first side of said layer of polyurethane material, said layer of knit fabric having interstices therebetween to absorb moisture; and a bottom layer of a knit fabric adhesively secured to a second side of said layer of polyurethane material.

2. The surgical drape of claim 1 wherein said drape has a thickness of between 0.015 inches and 0.034 inches.

3. The surgical drape of claim 2 wherein said polyurethane layer is a microporous polyurethane having a uniform pore size of 1 micron.

4. The surgical drape of claim 1 wherein said top layer is formed of a polyester warp knit fabric, said fabric having interstices therebetween to absorb, in liquid, at least 70% of its initial weight.

5. The surgical drape of claim 1 wherein said polyurethane layer has a thickness of between 20 $\mu$m and 30 $\mu$m.

6. The surgical drape of claim 4 wherein said top layer of a knit fabric and said bottom layer of a knit fabric are easily secured to said polyurethane material by means of a finely dispersed polyurethane adhesive.

7. The surgical drape of claim 1 wherein said drape has a weight of between 4.5 and 5.5 ounces per square yard.

* * * * *